United States Patent [19]

Lonker et al.

[11] Patent Number: 5,136,684
[45] Date of Patent: Aug. 4, 1992

[54] HEATING DEVICE FOR VOLATILIZATION OF FRAGRANT GEL

[75] Inventors: Lon M. Lonker, Marlton, N.J.; Enrico Zobele, Trento, Italy

[73] Assignee: Certified Chemicals, Inc., Cinnaminson, N.J.

[21] Appl. No.: 771,072

[22] Filed: Oct. 2, 1991

[51] Int. Cl.⁵ .................................................. A61L 9/03
[52] U.S. Cl. .................................... 392/392; 392/390
[58] Field of Search ............... 392/392, 390, 403; 219/436, 438, 521

[56] References Cited

U.S. PATENT DOCUMENTS

| | | | |
|---|---|---|---|
| 2,513,919 | 7/1950 | Costello | 392/392 |
| 2,931,880 | 4/1960 | Yaffe | 392/390 |
| 3,748,438 | 7/1973 | Costello | 392/392 |
| 4,214,146 | 7/1980 | Schimanski | 392/390 |
| 4,391,781 | 7/1983 | van Lit | 392/390 |
| 4,837,421 | 6/1989 | Luthy | 392/390 |
| 4,849,606 | 7/1989 | Martens | 392/390 |

*Primary Examiner*—Teresa J. Walberg
*Attorney, Agent, or Firm*—Seidel, Gonda, Lavorgna & Monaco

[57] ABSTRACT

A device for heating a fragrant gel is assembled from a base plate and a tray holder adapted to hold a gel cartridge. Electrical terminal prongs connect to a heating element which is disposed in an elongated channel in the base plate. The tray holder has a complimentary elongated channel, such that the heating element is completely sealed and electrically insulated when the holder is joined to the plate. The opposite convex side of the channel forms an elongated rail in the holder which acts both as a heat-distribution and a cartridge retaining member.

5 Claims, 2 Drawing Sheets

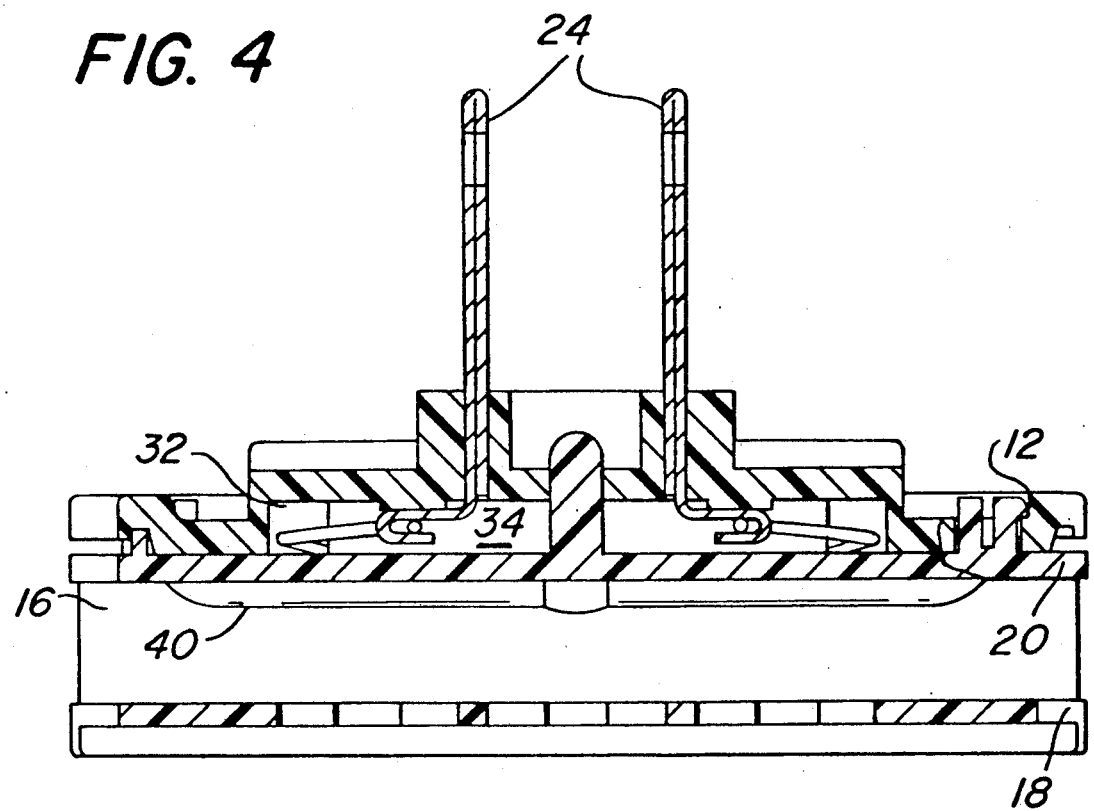
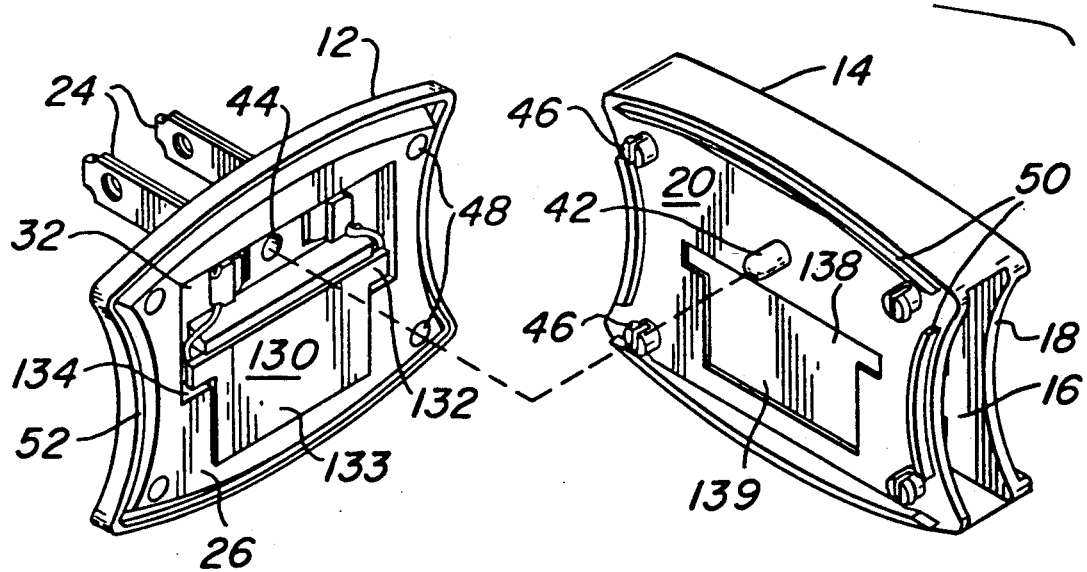

HEATING DEVICE FOR VOLATILIZATION OF FRAGRANT GEL

TECHNICAL FIELD

This invention is related to the general field of devices which release an aromatic vapor from a volatile carrier material by warming the material. In particular, it is related to air fresheners of the type intended to be plugged into an electrical outlet and slowly release fragrant vapor from a volatile gel.

BACKGROUND ART

There is great variety in the devices which are intended to plug into an electrical outlet to heat a volatile substance to release an aromatic vapor as a freshener scent, insect repellant or disinfectant. Some of the variety is related to the problem that electrical outlets may orient the receptacle plugs vertically or horizontally. It is preferable for the device to keep the volatile material above the heating element and from falling out of the insert slots. Thus, several prior art devices are directed to means which make them adaptable for either plug arrangement.

As an early example, U.S. Pat. No. 2,513,919 (Costello) discloses a plug-in vaporizer in which the inlet and exhaust air louvers are arranged at an angle with respect to the plug pins such that the louvers stay in the same vertical relationship whether the plug receptacle are horizontal or vertical. U.S. Pat. No. 2,611,068 (Wellens) discloses a vaporizer where the plug pin assembly can be rotated for the same purpose. U.S. Pat. No. 2,691,716 (also Wellens) discloses a vaporizer in which there are four slots, one at each corner, and cross ribs associated with each slot to define a compartment into which a volatile tablet may be inserted. A resistive heating element lies between the four compartments. Thus, whether the plug recepticals are horizontal or vertical, at least two of the four slots are upright, with their tablet compartments located above the heating element.

Another problem which has produced variations in plug-in vaporizers involves providing the proper temperature and distribution of heat to various compositions and shapes of volatile material. Two prior patents by one of the inventors of the present invention are illustrative of the problem and solutions found in the past. The first aspect of the problem is that a volatile tablet containing an insecticide, for example, may have a different composition and hence a different temperature for its optimum evaporation rate, than a tablet containing a perfume. U.S. Pat. No. 4,467,177 (Zobele) discloses a device which addresses this problem by providing two separate heating platforms, one further from the heating element than the other, to accommodate dissimilar materials which need different temperatures to stay within their desired volatility range. The second problem is the desire to distribute heat relatively evenly over a wide area of the material, which implies some form of heating plate. U.S. Pat. No. 4,251,714 (Zobele) describes the deficiencies in several prior types of heating plate, involving insufficient insulation, need for a grounding prong, and difficulty of assembly; and provides a solution by a T-shaped support housing a longitudinally extending heating element. An aspect of the present invention has similarities to the embodiments of that device.

Recently, gelled liquids containing fragrance oils have become used as room air-fresheners. Such material can be made slowly-volatile at room temperature and can be sealed in a container until ready for use. It can also be made such that the desired volatility is reached at a temperature slightly higher than normal room temperature, a plug-in electric resistance heater. A gelled air freshener of this type is sold under the trade name "GLADE PLUG INS". A container for such gel material which can be used in a plug-in heating unit is disclosed in U.S. Pat. No. 4,849,606.

With gel material air fresheners, the material is usually provided in replaceable, generally rectangular cartridges of approximately 1.5 inch length, 1 inch width, and 0.3 inch depth. A cartridge is inserted into a holder with a hollow chamber generally conforming to the shape of the cartridge. A resistive heating element connected to electrical outlet plug pins supplies heat to warm the material to its desired volatility temperature.

The size and shape of such cartridges and the composition of the gel material again present the problems of adaptability for vertical and horizontal plugs, even heat distribution, and ease of assembly. Consequently, an object of the present invention is to provide an improved heating device for use with a gel air-freshener. Various aspects of this objective and its achievement will be apparent from the detailed description of the best mode. For purpose of facilitating casual review, the following section briefly summarizes the invention in readily understood terms. However, the reader is cautioned that the full extent of invention is only apparent from reading the claims.

SUMMARY DESCRIPTION OF THE INVENTION

A device for heating a fragrant gel is assembled from a base plate and a tray holder adapted to hold a gel cartridge. Electrical terminal prongs connect to a heating element which is disposed in an elongated channel in the base plate. The tray holder has a complimentary elongated channel, such that the heating element is completely sealed and electrically insulated when the holder is joined to the plate. The opposite convex side of the channel forms an elongated rail in the holder which acts both as a heat-distribution and a cartridge retaining member.

In a preferred embodiment, the channels are located essentially along the longer centerline of the rectangular interior of the holder, and the holder is open at the two width ends to allow a cartridge to be inserted from either side.

When intended for use with a standard sized replacement cartridge, the terminal prongs are preferably located near the top center of a long side of the rectangle and are spaced apart along a line parallel to the long side. This arrangement allows use with a standard-sized double-receptacle electrical outlet without blocking the unused receptacle, whether the recepticals are arranged vertically or horizontally.

BRIEF DESCRIPTION OF THE DRAWINGS

For the purpose of illustrating the invention, the drawings show one or more forms which are presently preferred; it being understood, however, that this invention is not limited to the precise arrangements and instrumentalities shown.

FIG. 4 is a section view of the device shown in FIG. 1 along the line and in the direction indicated by the arrows 4—4.

FIG. 5 is an exploded view of an alternative embodiment of a heating device according to the invention, wherein the base plate is shown separated from the holder.

BEST MODE FOR CARRYING OUT THE INVENTION

Figure 1:
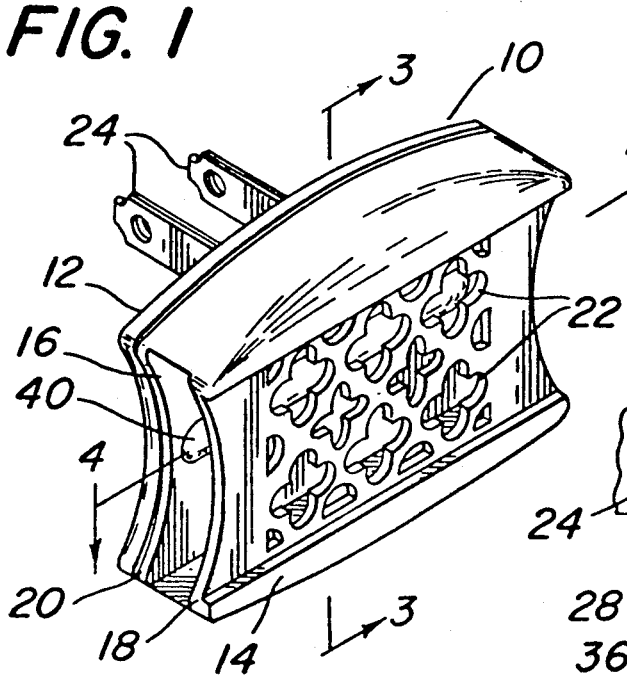
FIG. 1 is a perspective view of a heating device according to the invention.

FIG. 1 shows an assembled heating device 10 according to the present invention. The device is intended to be used with a disposable and replaceable cartridge containing volatile gelled material with an aromatic substance which is released as a vapor when the material volatizes.

Such cartridges are normally sold with a seal over the gel material. When the seal is removed, the cartridge serves a tray for the material as it undergoes heating and vaporization. Although a cartridge is not depicted in the drawings, its function will be understood from this description and the background information mentioned above.

For purposes of brevity, this discussion will refer only to using of a gel material with perfumed fragrance as a room air freshener; it being understood that the heating device of this invention could be used as well with a gel containing insecticide, disinfectant, or other substance.

The device 10 is formed by joining a generally flat base plate 12 to a tray holder 14. The holder is adapted to receive and enclose a generally rectangular tray containing a slowly volatile fragrant gel, as described above. Thus, the holder 14 includes a generally rectangular hollow body 16 defined in part by a front panel 18 and a back panel 20 which are spaced apart by substantially the depth of a gel tray. The front panel has a lattice of vents 22 to release fragrant vapor out of the holder.

Figure 3:
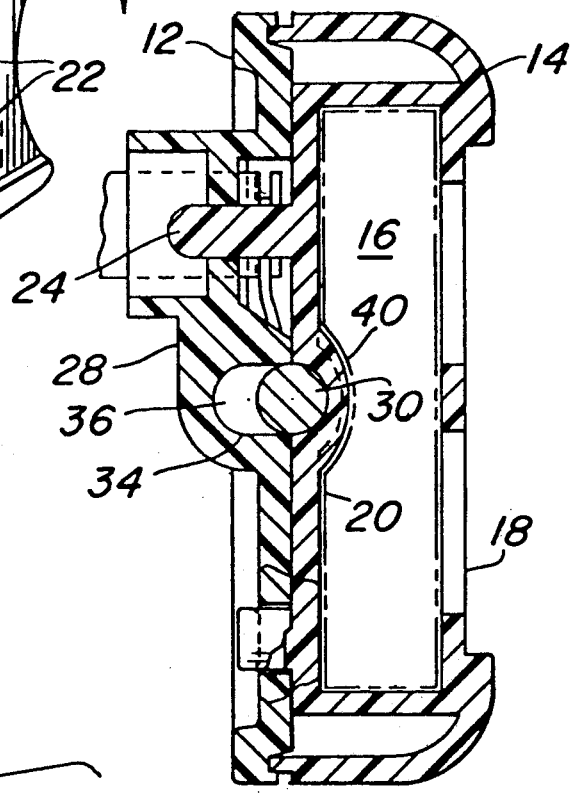
FIG. 3 is a section view of the device shown in FIG. 1 along the line and in the direction indicated by the arrows 3—3.
Figure 2:
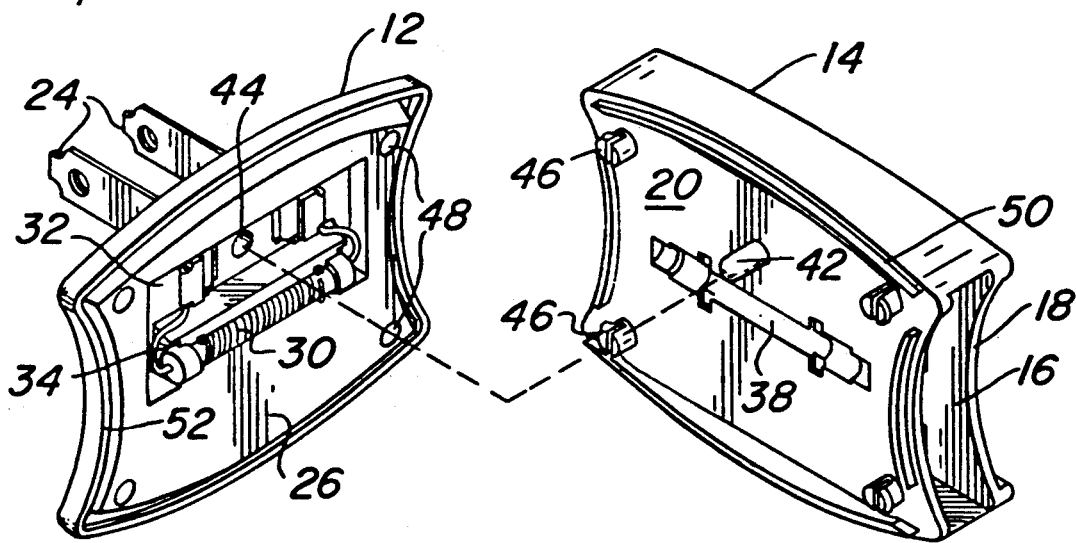
FIG. 2 is an exploded view of the device shown in FIG. 1, wherein the base plate is shown separated from the holder.

As best seen in FIG. 2, the base plate 12 has electrical terminal prongs passing through from its inner face 26 to its outer face (28 in FIG. 3). An electrical resistance heating element 30, (cylindrical in this embodiment), is housed in a chamber 32 in the base plate and is connected to the terminal prongs 24 by appropriate connector tabs and lead wires. Thus, the heater element 30 receives electrical current to generate resistance heating when the prongs are plugged into an electrical outlet. The heating element is mounted in an elongated channel 34 formed in the chamber 32 and oriented such that the channel's open side faces away from the outer face 28. Preferably, the heater element is snapped into retaining tabs which hold it such that the channel mouth is aligned with a cross sectional diameter of the element, so that the element 30 is "half-in" the channel 34, as shown in FIG. 3. The channel is preferably deeper than a radius of the heater element, so that a dead air space 36 exists behind the element. This arrangement provides heat insulation between the base plate and the element and space for the element lead wires to lie inside the chamber when the base plate is joined to the holder.

As shown in FIG. 2, the back panel 20 of the holder has a mating semi-cylindrical channel 38 oriented such that the open mouth of the channel faces away from the front panel 18, and which is intended to enclose the exposed half of the heater element 30 when the holder is joined to the base plate (as shown in FIG. 3). The holder, as stated above, contains a generally rectangular hollow body 16 to receive a rectangular tray. The channel 38 extends substantially along the longer centerline of the back panel. On the opposite side of the panel 20, the channel produces a raised rail 40 also extending along the longer centerline of the rectangular body.

As known to those in the art, disposable gel cartridges normally have a centerline key slot in the bottom of the tray to guide it into the holder and to help retain it. Thus, the rail 40 guides and retains a cartridge by entering the key-slot when the cartridge is inserted and raising the cartridge to a snug fit against the front panel 14. However, as the heating element 30 is also disposed under rail 40 and within the closed compartment formed by channels 34 and 38, the rail 40 further acts as a heating plate to distribute heat relatively evenly along the length of the tray.

The base plate 12 and holder 14 are fabricated as separate pieces for ease of assembling and connecting the heater element, but are later bonded together with the base plate being joined to the holder such that the inner face of the base plate is in flush alignment against back panel of the holder, and with the channels aligned to enclose the heating element. To facilitate this joinder, the back panel 38 may have an alignment dowel 42 disposed to be inserted into a bore 44 between the prongs in the base plate, and four split posts 46 disposed roughly at each corner of the panel to be inserted through corresponding bores 48 in the base plate. For purposes of forming a seal against water and dirt, the back panel may be provided with sealing ridges 50 and the base plate with a matching perimeter groove 52 into which the ridges may be pressed. After the base plate and holder are pressed together, they may be permanently bonded by heat welding the split posts 46.

Turning now to FIG. 5, the heating element 130 is a positive thermal coefficient (PTC) element shaped as an elongated strip portion 131 and a plate portion 133, rather than the cylindrical shape of element 30 in the previous embodiments. PTC elements are known in the art to be useful in heating devices because they exhibit a maximum temperature at which current flow begins to limit. The chamber 132 is extended to accept the contour of the plate portion 133, and a conforming chamber 139 is contiguous with the channel 138 in the back panel 20. The plate portion 133 distributes heat over a wide area to the gel.

In both the embodiments, the plug prongs 24 are preferably located in the base plate near the top center of a long side of the rectangular body 16, and are spaced apart along a line parallel to the long side, as shown in FIGS. 2 and 5. This arrangement allows use with a standard-sized double-receptacle electrical outlet without blocking the unused receptacle, whether the recepticals are arranged vertically or horizontally. The replacement cartridges, as previously described, are typically 1.5×1.0 inches. Plug prongs are 0.5 inches apart, and double receptacle outlets space the plug recepticals 1 inch apart. Thus, by placing the prongs centered on the long side (1.5 inch)of the rectangle, the cartridge will extend only 0.5 inch past each prong, allowing up to the additional 0.5 inch for molding or contour of the holder 14 before it will interfere with the adjacent receptacle. By contrast, the device shown in U.S. Pat. No. 4,849,606 locates the prongs centered on the short side of the rectangle, such that the holder extends well over 1 inch from the prongs to enclose the 1.5 inch cartridge, and blocks the adjacent receptacle.

Further, the holder 14 has equal sized openings at the shorter side of the rectangular body for insertion of the cartridge from either direction. The molding 54 of the holder which surrounds and encloses the panels 18,20 may be of a aesthetically pleasing design, such as the convex portion over the long sides and the concave portion at the short side openings, as shown in the drawings. The molding is preferably integral with the holder. The holder and base plate may preferably be made of an injection moldable thermoplastic material.

Industrial Applicability

The heating device of this invention is expected to be marketed primarily as a home air freshener. It may be used with a variety of disposable gel cartridges of different manufacture and scent fragrances having the standard rectangular dimensions.

I claim:

1. A heating device for volatilization of a fragrant gel, comprising:

(a) a generally flat base plate having an outer face and an inner face, with electrical outlet terminal prongs passing through from inner to outer face, said inner face having an elongated channel oriented such that the open side of the channel faces away from the outer face;

(b) an electrical resistance heating element housed in said channel and connected to said terminal prongs to receive electrical current when the prongs are plugged into an electrical outlet;

(c) a holder adapted to receive and enclose a generally rectangular tray containing a slowly volatile fragrant gel, said holder comprising a generally rectangular hollow body defined in part by a front panel and a back panel spaced apart by substantially the depth of the gel tray, said front panel having a lattice of vents to release fragrant vapor from the body, and said back panel having an elongated channel extending substantially along the longer centerline of the back panel and oriented such that the open side of the channel faces away from the front panel; and (d) the base plate being joined to the holder such that the inner face of the base plate is in flush alignment against back panel of the holder, and the elongated channels are aligned to enclose the heating element.

2. A heating device as in claim 1 wherein base plate is joined to the holder by joining means comprising a plurality of posts on the back panel of the holder adapted to be inserted through matching bores in the base plate and thermally welded to the base plate.

3. A heating device as in claim 2 further comprising said base plate having a perimeter channel on its inner face extending generally around the circumference of the base plate adjacent the edge of the inner face, and said back panel having one or more raised elongated ridges adapted to be pressed into said channel.

4. A heating device as in claim 1 wherein the holder has opposite open sides between front and back panels adapted to receive a tray inserted from either side.

5. A heating device as in claim 3 wherein the holder has opposite open sides between front and back panels adapted to receive a tray inserted from either side.

* * * * *